United States Patent
Hofmann et al.

(10) Patent No.: US 6,446,679 B2
(45) Date of Patent: Sep. 10, 2002

(54) METHODS AND APPARATUS FOR PACKING CHROMATOGRAPHY COLUMNS

(75) Inventors: Martin J. Hofmann; Gordon R. Thorn, both of Gloucestershire (GB)

(73) Assignee: Euroflow (UK) Limited, Gloucester (GB)

( * ) Notice: Subject to any disclaimer, the term of this patent is extended or adjusted under 35 U.S.C. 154(b) by 0 days.

(21) Appl. No.: 09/731,172

(22) Filed: Dec. 6, 2000

Related U.S. Application Data

(63) Continuation of application No. PCT/GB99/01815, filed on Jun. 8, 1999.

(30) Foreign Application Priority Data

Jun. 8, 1998 (GB) .............................................. 9812344

(51) Int. Cl.[7] .............................................. B65B 1/04
(52) U.S. Cl. ................................ 141/1; 141/4; 141/67; 141/70

(58) Field of Search ............................... 141/1, 4, 5, 67, 141/46, 285, 286, 70, 71

(56) References Cited

U.S. PATENT DOCUMENTS

| 4,597,421 A | * | 7/1986 | Wells |
| 5,222,529 A | * | 6/1993 | Zoltan et al. |
| 5,241,998 A | * | 9/1993 | Ashraf-Khorassani |

* cited by examiner

*Primary Examiner*—Steven O. Douglas
(74) *Attorney, Agent, or Firm*—Pearne & Gordon LLP

(57) ABSTRACT

Particulate chromatography medium such as silica is packed into a chromatography column (2) along a feed conduit (16, 18) leading to a packing port (1) through the column wall. A motive flow of a liquid packing vehicle such as a non-polar organic solvent is established along a feed conduit by a pump (111). The medium, for example silica which is poorly compatible with low-polarity vehicles, is easily entrained in the motive flow by introducing it into the feed conduit (16, 18) via an ejector (30). This avoids subjecting the medium to the action of a mechanical pump.

12 Claims, 6 Drawing Sheets

METHODS AND APPARATUS FOR PACKING CHROMATOGRAPHY COLUMNS

This application is a continuation of application Ser. No. PCT/GB99/01815, filed Jun. 8, 1999.

FIELD OF THE INVENTION

This invention relates to methods and apparatus for packing chromatography columns with the particulate medium used for chromatography.

BACKGROUND

It is no simple matter to pack particulate chromatography media into chromatography columns, particularly the large columns (e.g. from 100 mm up to as much as 2000 mm and beyond in diameter) used in industrial-scale preparative chromatography. Typical requirements are that the packed bed be continuous, uniform, fill the column space entirely and be sufficiently initially compressed not to shift under the fluid flow conditions prevailing subsequently during chromatography. An improperly packed bed is practically useless and has serious cost implications having in mind the usually high value of products purified using chromatography.

The conventional method of packing a column is to remove the top wall (end plate or piston) of the column and pour in the medium as a slurry in a suitable liquid vehicle. The vehicle flows down through the separation filter (sinter) at the foot of the column and away through a waste port, while the bed of solid medium (e.g. silica) gradually accumulates to fill the column space. This is a skilled and time-consuming task.

For this reason the use of automated packing by way of a packing port through the column wall has recently been preferred. The packing port, fed with a slurry of the medium via a feed conduit, may be a hole with a simple open/shut control. It is known for example to open and shut the hole vis à vis the column interior using a piston-fashion movement of the column end cell to cover and uncover it. The packing port may have a nozzle or a more sophisticated nozzle or spray nozzle arrangement. See for example GB-A-2258415 and WO-A-96/10451. These describe arrangements in which slurry enters the column space at a spray nozzle having an array of spray holes to distribute the incoming flow. Another feature is that the nozzle projects from the column wall into the column space, at least at the time of spraying the slurry. The present proposals are preferably used with spray nozzle arrangements having one or both of these features.

The introduction of slurry through a restricted packing port raises a number of important practical requirements, largely associated with the need to feed the slurry at substantial pressure in order to achieve a flow rate adequate to distribute the slurry and pack the bed down. Depending on the circumstances various difficulties can arise, including inadequate levels of packing, damage to the media particles (especially with large particle sizes), and separation of the slurried particles from the liquid slurrying vehicle in the pressurised feed system.

SUMMARY OF THE INVENTION

The present proposals aim to provide new and useful methods and apparatus for packing particulate chromatography media into chromatography columns through a packing port in the column wall, preferably through a nozzle or spray nozzle.

In general terms what we propose is to establish a pressurised motive flow of liquid vehicle along a feed conduit leading to the packing port, typically by means of a pump, and to introduce a separate flow of the particulate medium into the feed conduit to be entrained in the motive flow. The medium is preferably introduced into the feed conduit as a dispersion in a liquid vehicle, which may be the same as that used for the motive flow.

The motive flow of liquid vehicle can then be substantially or entirely free of particulate medium upstream of the flow junction at which it entrains the medium.

Because the motive flow can provide the pressure necessary for packing, the introduced flow of particulate medium can be at a lesser pressure head. This avoids the need to subject the medium itself to pumping at packing pressure, with possible mechanical degradation of the particles, or to any pumping at all, and may enable better packing results particularly with large-particle media which are most liable to be damaged in a pump.

A further specific advantage can be achieved in cases where the medium and liquid vehicle are poorly compatible. This may arise in particular where one or more of the following apply:

the medium and liquid vehicle are widely different in polarity;

the medium particles are large;

the liquid vehicle is of low viscosity.

An example is a slurry of normal-phase silica in organic solvent, especially non-polar organic solvent. We find that our techniques can enable effective packing of medium/vehicle combinations which, if pumped as slurry, will separate. This is valuable because of the general demand for a wide choice of solvents as eluents in chromatography; it is highly preferred to slurry the packing using the same solvent.

However the method is useful for a wide range of media. For example it can avoid subjecting soft or brittle media to the action of a mechanical pump. Possible media include rigid, semi-rigid and softer media such as all silicas, polystyrenedivinylbenzene, polymethacrylates, agarose, dextran and cellulosic media.

We prefer to introduce the flow of particulate medium into the established pressurised motive flow at a reduced-pressure zone of the feed conduit, and most preferably at by means of an ejector (jet pump) provided therein. The ejector is a well-known fluid pumping arrangement in which a flow of a motive fluid at a higher pressure is used to pump another fluid at a lower pressure—conventionally called the suction flow—at some intermediate resultant discharge pressure. An ejector typically has a relatively restricted nozzle at which a fast flow of the motive fluid emerges into a larger cross-sectional area region where it can accelerate the suction flow; normally this is followed by a gradual increase of cross-sectional area (a diffuser) to restore the pressure of the combined flows by reducing the kinetic energy. The fluid mechanics and practical implementation of ejector operation are well established and need not be discussed in detail.

By thus exploiting a low-pressure zone in the motive feed conduit, a supply of particulate medium can be entrained from a medium source having a passive or non-pumped feed, e.g. under gravity. It may be drawn up against a negative pressure head.

It is preferred that liquid vehicle emerging from the column during packing is recycled to the packing process. The process is apt to introduce the medium at a high slurry dilution and recycling helps to reduce the overall volume of liquid vehicle required.

A continuous (steady) output pump such as a centrifugal pump is preferred as the motive device because it can provide a steady drawing pressure for the packing medium; pulsing pumps such as diaphragm pumps will work but are less preferred.

Aspects of the invention include methods as described and also apparatus adapted to carry out such methods. Such apparatus may comprise for example a feed conduit connected at an upstream end to a pump or other fluid flow motive means, and at its downstream end having a connector for connection to a slurry spray nozzle or other slurry port provided through the wall of a chromatography column. A medium conduit meets the feed conduit at an intermediate junction thereof, for introduction of particulate medium—preferably as a slurry of the medium in liquid vehicle—to be entrained in the pressurised flow of liquid vehicle passing along the feed conduit from the motive means. The junction preferably comprises means such as an ejector for providing a low-pressure zone as described above, helping to draw the flow of medium into the pressurised flow.

The apparatus may further include one or both of a liquid vehicle supply vessel connected to the motive means and a medium supply vessel connected to the medium supply conduit, preferably directly without any mechanical motive means. Desirably means are provided for feeding liquid vehicle back to the medium supply vessel. Means for agitating the vessel contents to maintain the slurry are usually provided. This may be by hydraulic mixing, e.g. feeding a recycled liquid flow up into the bottom of the container to create turbulence, and/or a mechanical agitator for stirring or agitating the contents of that vessel to maintain slurry therein may be used. The apparatus may include a recycle line for returning liquid vehicle to one or both of the liquid vehicle supply vessel and the medium supply vessel after it has passed through the column during packing. This can reduce the volume of liquid used. It can also enable a smaller supply vessel to be used because slurrying-up is ongoing and the medium can be added in convenient increments. One or more chromatography columns, each having the spray nozzle or other packing orifice and an outlet for liquid vehicle which has flowed through the column from the packing orifice, may also be included in the apparatus. Elements of the apparatus may be mounted on a common frame which preferably is mobile i.e, as a trolley or 'skid' so as to be movable to and from a column needing to be packed.

BRIEF DESCRIPTION OF THE DRAWINGS

Embodiments of the invention are now described by way of example and will make reference to the accompanying drawings in which.

DETAILED DESCRIPTION OF TRIALS AND EMBODIMENTS

Figure 1:
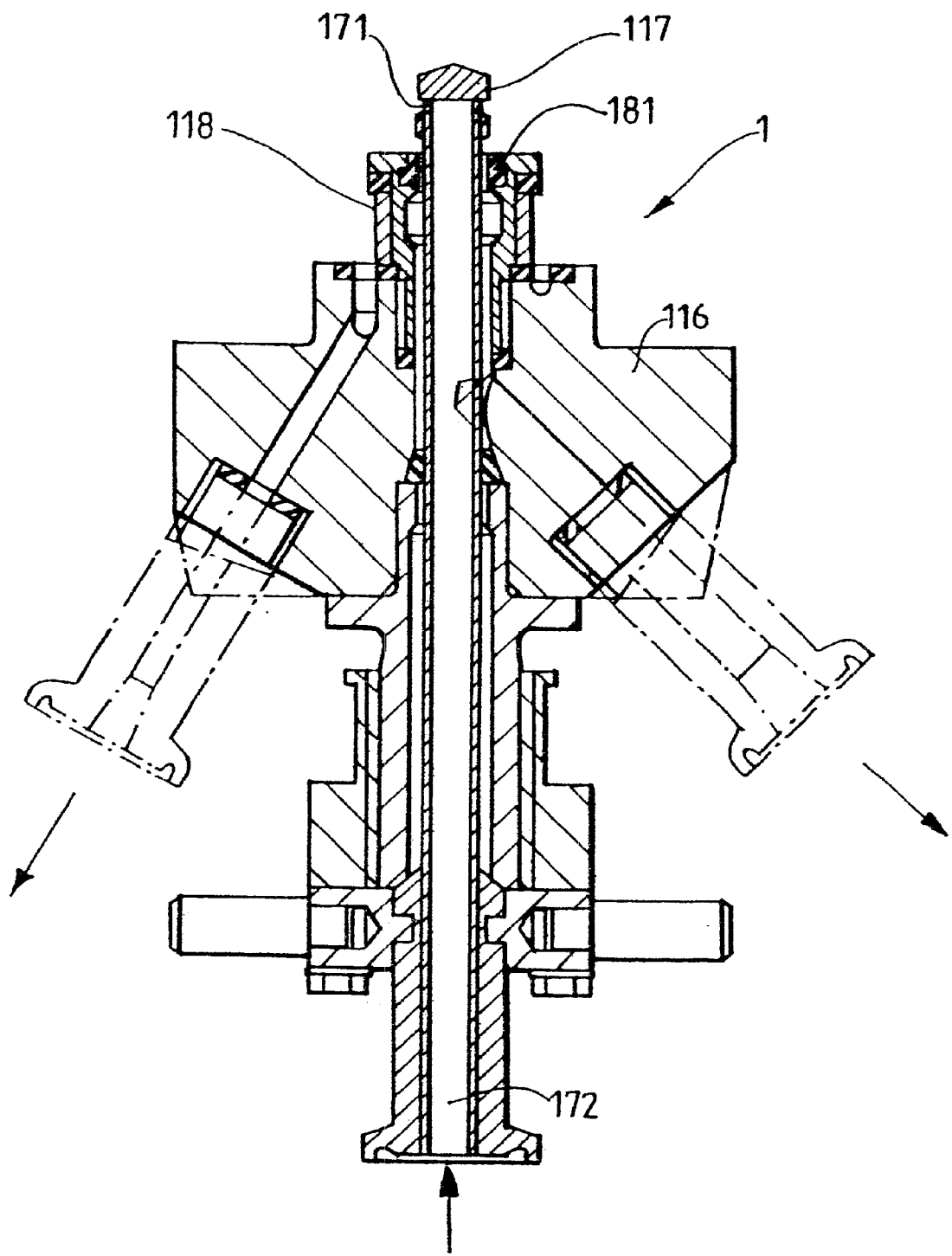
FIG. 1 is a schematic axial cross-section of a packing nozzle used in the experiments.
Figure 2:
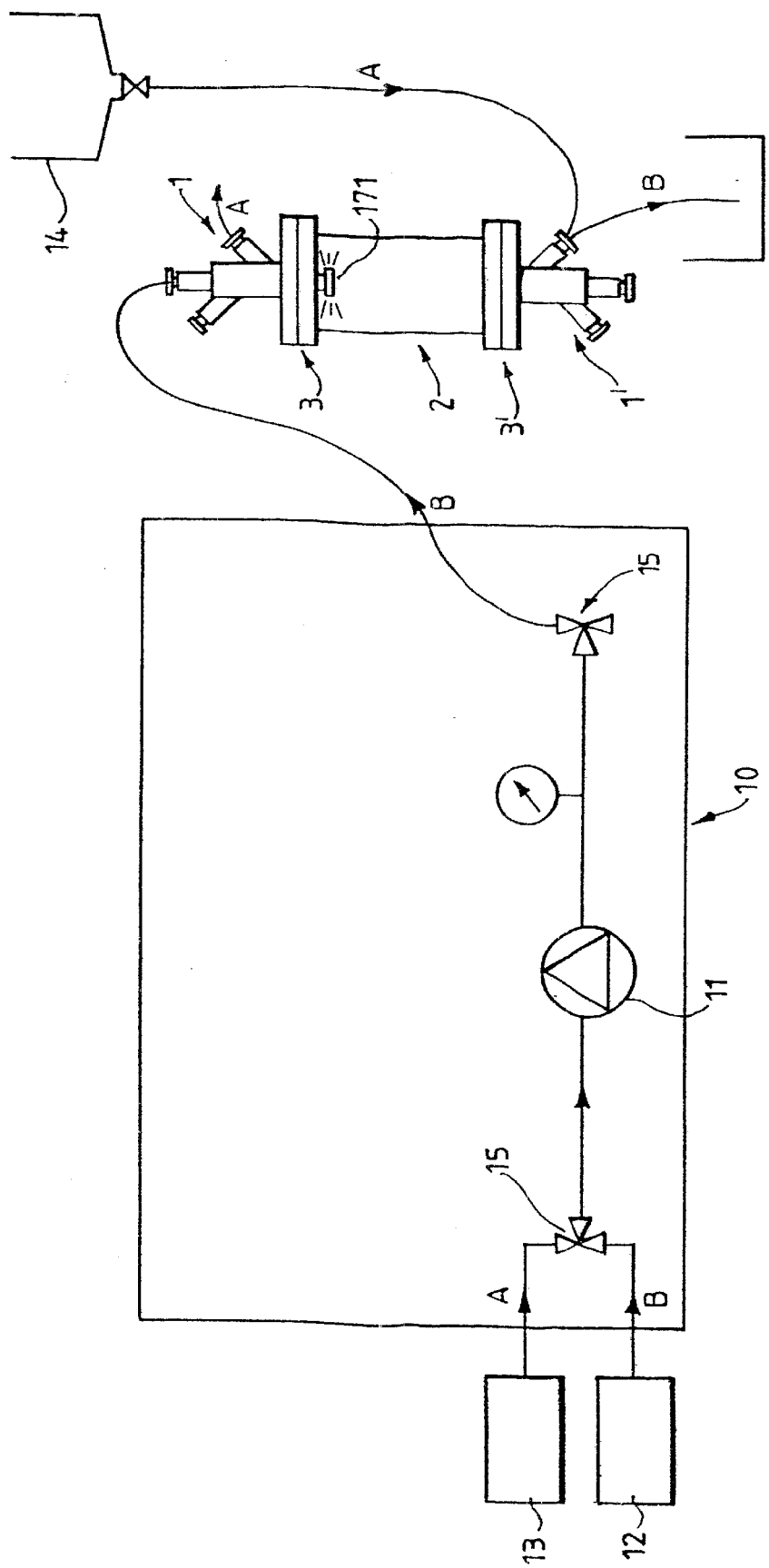
FIG. 2 shows schematically a simple packing system used for comparative trials.

Refer firstly to FIGS. 1 and 2. FIG. 2 shows the general layout of a trial packing system, with a chromatography column 2 on the right of the figure being of a generally well-known type with upright cylindrical housing, top and bottom end cells 3, 3' and packing/flow nozzles 1, 1' installed through the end cells. Vessels to supply and receive liquid flows to and from the column 2 will be described in turn. A packing station 10 includes a pump 11 connectable via control valves 15 selectively to reservoirs 12, 13 of medium slurry and liquid vehicle (solvent). The general principles for construction of a packing station with pump (s), pipework, valves, seals and so forth of materials appropriate to the separation system are routine knowledge in the art.

The particular project is to use dichloromethane ($CH_2Cl_2$) as a liquid vehicle for packing the column and subsequently as eluent (mobile phase) for chromatography in conjunction with a normal-phase silica medium. The trial medium was Amicon's "Matrex" (trade mark) of particle size 70 to 200 μm; a relatively large particle size.

The first part of the trial was to pack the silica medium as a slurry in the $CH_2Cl_2$ through the nozzle 1 into the column. This technique is in itself known.

FIG. 1 shows the preferred nozzle used, corresponding to WO-A-96/10451 to which reference can be made. The exact particulars of the nozzle are not critical for the present discussion. It has a module 116 mounted through the end cell of the column, with a central armature 117 movable relative to a surrounding nozzle sealing structure 118 between packing and unpacking positions. In the position shown the tip of the armature nozzle 117 projects clear of the surrounding seal structure 118. The armature 117 is a hollow tube and slurry can be pumped along its central conduit 172 to emerge from the spray nozzle openings distributed around its tip. The nozzle can be moved to a closed condition—in this embodiment, by retraction of the nozzle armature 117—so that seals 181 around the mouth of the sealing sleeve 118 close off the spray nozzle from the interior of the column.

In the position shown, fluid can escape from the column space through the annular clearance between the central armature 117 and the surrounding sealing sleeve 118. This is useful also for unpacking, when solvent alone rather than slurry is pumped in through the nozzle to disperse an existing bed. Packing can be done in this position too, by pumping in slurry, but the particular version of the nozzle shown enables an intermediate position (not shown) in which the seals 181 engage the lower port of the armature tip so that the spray nozzles remain open but escape of liquid around the armature, to the waste slurry outlet port, is prevented. Further details of packing nozzle constructions and their use will be found in GB-A-2258415 and WO-A-96/10451. The virtues of using nozzles by comparison with the traditional method are now established.

Trial 1

As an initial stage the column and pipework was primed (flows indicated "A") by pumping $CH_2Cl_2$ into the pumping station from a first $CH_2Cl_2$ tank 13, and up through the column by gravity feed from a raised $CH_2Cl_2$ tank 14. Outflow was from the mobile phase port of the top nozzle 1.

34 kg of the Matrex silica was slurried up with 100 liters of $CH_2Cl_2$ in the slurry reservoir 12, connected to the packing station pump 11.

The parameters of the system were as follows. $CH_2Cl_2$ is a dense, low viscosity (0.4 cp) solvent. A stirrer was used in the slurry vessel to maintain the slurry. The dimensions of the column were 280 (diameter) by 1000 mm (length).

On activating the pump with the nozzle 1 in the packing position (flows "B") the column could not be packed. The low viscosity of the $CH_2Cl_2$, combined with its poor compatibility with the (relatively polar) silica, resulted in separation of the liquid from the slurried solid under the suction generated by the pump. These solid particles blocked the pipes and valves.

Trial 2

This used the same column as Trial 1, but the liquid vehicle was propan-2-ol, a more polar solvent which normally suspends silica and at 1.9 cp is more viscous than $CH_2Cl_2$. The slurry was made up in the same way.

Once again however the pump pulled the solvent off the particulate solid and the system was blocked, although less seriously than in Trial 1.

The large-particle silica is relatively difficult to hold in suspension under pumping conditions, making this a demanding test for the propan-2-ol which usually would be able to carry a normal-phase silica.

EMBODIMENTS OF THE INVENTION

Laboratory Trial

Figure 3:
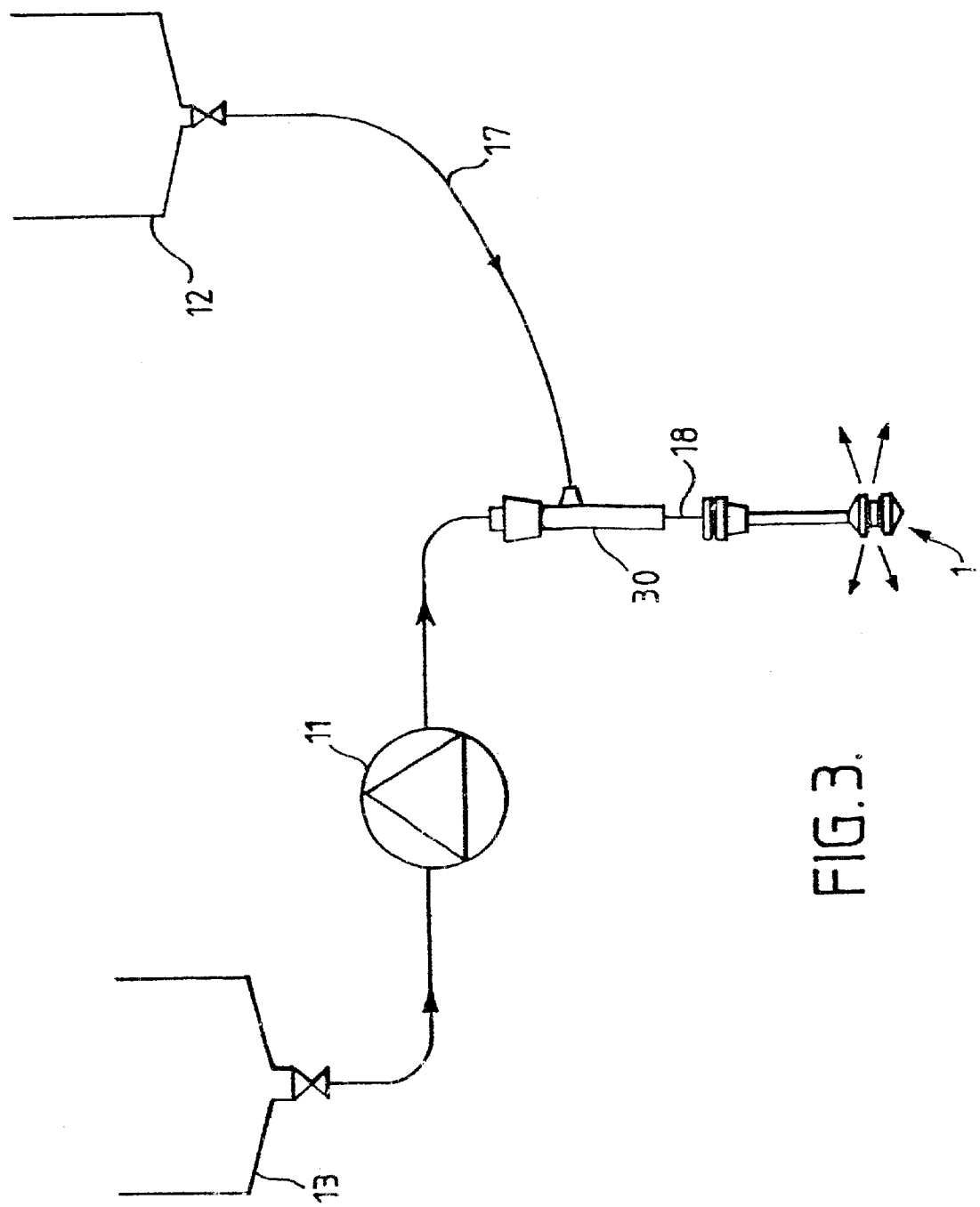
FIG. 3 is a diagrammatic representation of a small-scale trial system using an ejector pump for driving slurry.

We arranged a small-scale trial system to pump the slurry by means of an ejector, so that the slurry would not be subject to the action of the mechanical pump. See FIG. 3. The packing station 10 was generally the same as before, but no column was used; only an isolated packing nozzle 1. Only the $CH_2Cl_2$ vessel 13 was connected to the pump 11 (an air-driven double diaphragm pump, as before). The line 17 from the slurry vessel 12, containing the same Matrex silica slurried in $CH_2Cl_2$, was joined into the feed system downstream of the pump 11 at an ejector 30. The pump 11 provided the motive flow to the ejector and the slurry line 17 was connected as the suction flow. The slurry vessel 12 was raised above the system so that gravity would assist slurry flow into the ejector, and the slurry vessel stirred as before.

The ejector was a conventional commercial product made in polypropylene, obtained from Kartell.

A sample volume of slurry, with 500 g of dry silica in 3 liters of $CH_2Cl_2$, was put in the slurry vessel 12, and 16 liters of $CH_2Cl_2$ as motive fluid put in the other vessel 13 connected to the pump 11. The slurry was stirred continuously and the pump then allowed to run. All the slurry liquid was successfully sucked through into a collection vessel, and the flows were as follows.

| | |
|---|---|
| Suction Flow (slurry) | 1.7 liters/minute |
| Total Flow (after ejector; more dilute slurry) | 10 liters/minute |

The volume ratio of the suction flow to the motive flow using the ejector was therefore about 1:5. The flow of slurry drawn by the ejector was relatively constant over the period, and there was no problem with blockage of the system during pumping.

Full-scale Trial

Figure 4:
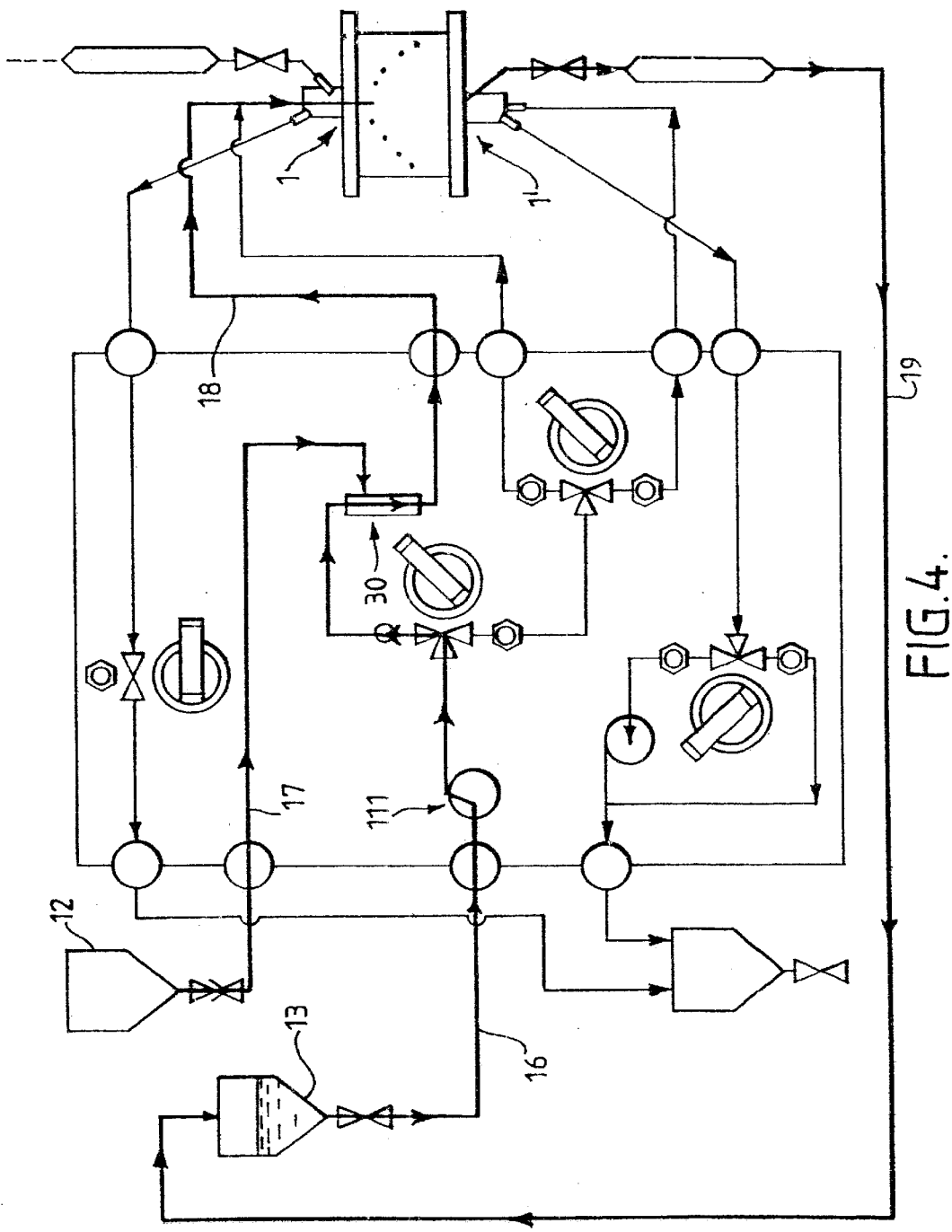
FIG. 4 is a diagrammatic representation of a larger-scale packing system.
Figure 5:
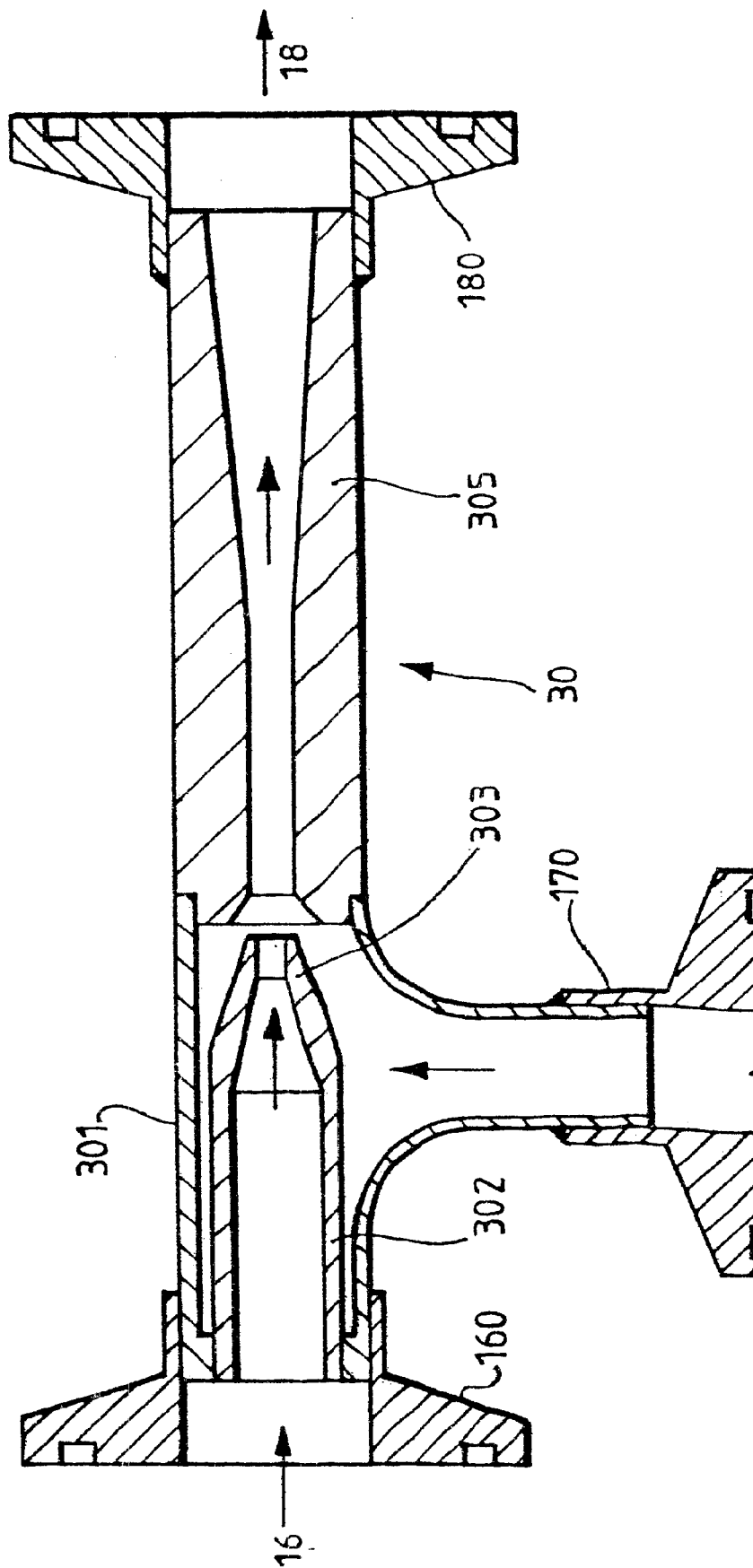
FIG. 5 is an axial cross-sectional view of an ejector pump which can be used in the FIG. 4 system.

The apparatus used can be seen in FIGS. 4 and 5. The conditions were more demanding than in the failed comparative trials above in that the same silica (60A Matrex) was used with the same $CH_2Cl_2$ liquid vehicle, but the columns were larger: 600 by 1000 mm stainless steel columns.

FIG. 4 is the diagram of the preferred packing arrangement. Only the characteristic features are discussed below; a skilled person will readily appreciate the other, more conventional features of the diagram.

In particular the system included a slurry vessel 12 and liquid supply vessel 13 as before, the former containing 175 kg of silica slurried in 600 liters of $CH_2Cl_2$ and the latter containing 600 liters of $CH_2Cl_2$.

The packing pump 111 installed in the section of pressurised liquid supply line 16 upstream of the ejector 30 in this embodiment was a centrifugal pump. A centrifugal pump has the advantage of a continuous output pressure as compared with the pulsating flow from a diaphragm pump.

In anticipation of using a high proportion of $CH_2Cl_2$ a liquid vehicle return line 19 was provided from the bottom nozzle 1' of the column back to the $CH_2Cl_2$ supply vessel 13.

Packing was then carried out in accordance with the following protocol.

| | STEP ACTION | TOP NOZZLE (1) POSITION | BOTTOM NOZZLE (1') POSITION |
|---|---|---|---|
| | PACKING | | |
| 1 | Fill the 1000–1300 liter slurry vessel 12 with 600 liters of dichloromethane | n/a | n/a |
| 2 | Slowly add 175 kg of the 70–200 um 60 A silica, stirring continuously with mechanical stirrer. Allow the silica to be fully wetted and degassed before continuing addition. | n/a | n/a |
| 3 | Allow the slurry to degas, leave at least 1 hour. | n/a | n/a |
| 4 | Prime the column from the 'Liquid Vessel' 13 containing 600 liters of dichloromethane. Pump dichloromethane into the bottom nozzle and out of the top mobile phase (MP) port. | Run (fully retracted) | Pack (mid position) |
| 5 | Once $CH_2Cl_2$ appears free of air at the top MP outlet, retract bottom nozzle and turn off pump. Close top MP valve. | Run (fully retracted) | Run (fully retracted) |
| 6 | Prime lines and top nozzle body with slurry, returning the Top Waste Port to the Slurry Tank 12. | Run (fully retracted) | Run (fully retracted) |
| 7 | Adjust valves to select flow paths shown bold in the figure, adjust pneumatic air flow to pump to 3 bar. Slurry is pumped into the column via the ejector 30. | Pack (mid position) | Run (fully retracted) |
| 8 | The ejector pressure should be 5 to 6 bar, the column pressure should be 0.5 to 1 bar, throughout the pack. | Pack (mid position) | Run (fully retracted) |
| 9 | When the column is fully packed the column pressure rises quickly to be approximately equal to the ejector pressure, 5–6 bar. | Pack (mid position) | Run (fully retracted) |
| 10 | Once packed, clean slurry lines by rinsing with $CH_2Cl_2$ from the motive liquid tank, include the ejector and nozzle valve. Close off MP valves. | Run (fully retracted) | Run (fully retracted) |

Figure 6:
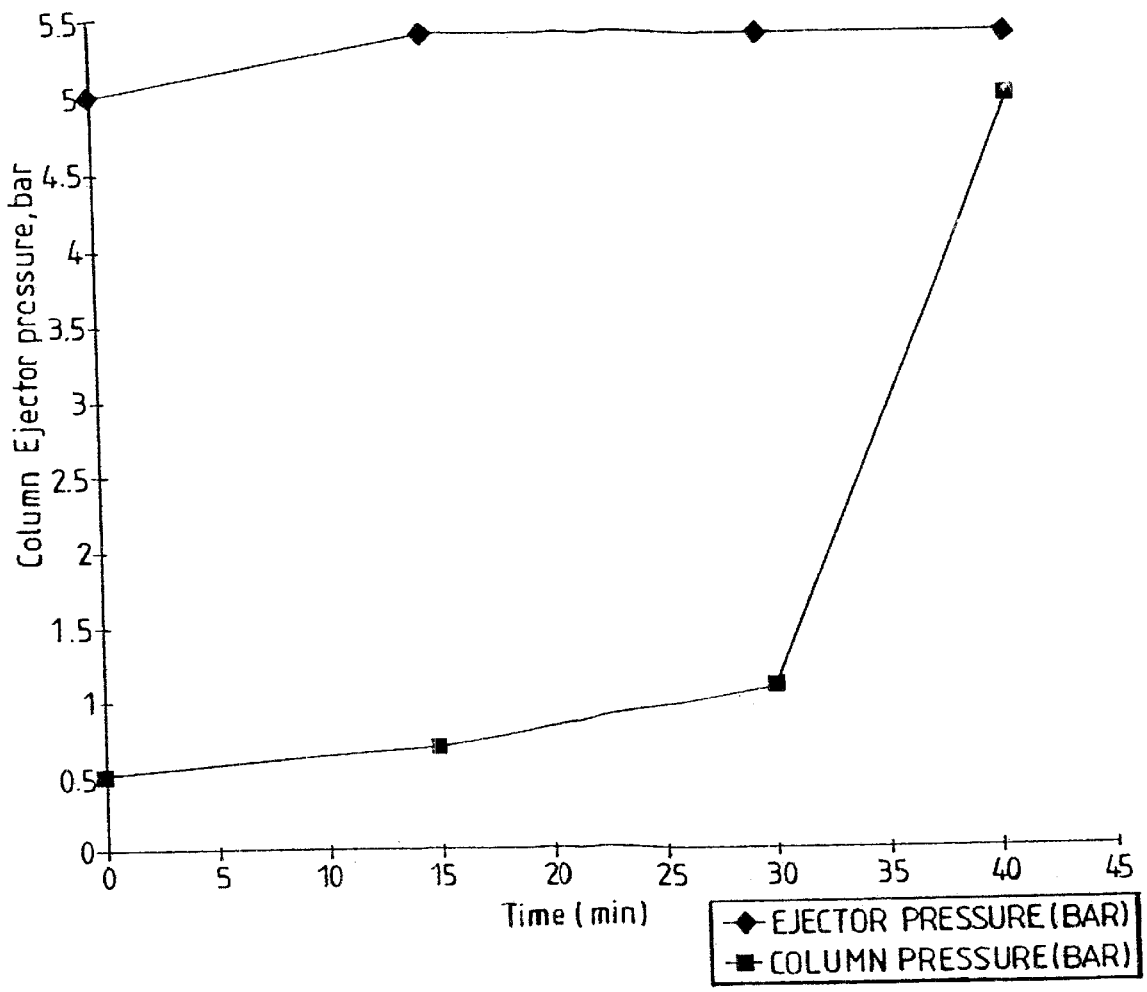
FIG. 6 is a graph indicating pressure variations at the ejector output and column as packing proceeds.

As packing proceeded we monitored the general behaviour of the system and in particular variations of the ejector pressure and column pressure with time. These data are shown below and plotted in FIG. 6.

| TIME (min) | EJECTOR PRESSURE (BAR) | COLUMN PRESSURE (BAR) | COMMENTS |
|---|---|---|---|
| 0 | 5 | 0.5 | Slurry volume |
| 15 | 5.4 | 0.7 | approx. 500l, air |

-continued

| TIME (min) | EJECTOR PRESSURE (BAR) | COLUMN PRESSURE (BAR) | COMMENTS |
|---|---|---|---|
| 30 | 5.4 | 1.1 | pressure 2.2 bar |
| 41 | 5.4 | 5 | PACKED |

We found that a sharp rise in column pressure to 5 bar, essentially the same as the ejector pressure, indicated that the column was fully packed. At this point the pump was turned off and the packing nozzle retracted. The column was then run with a test chromatography process and the packed bed found to function satisfactorily.

As packing proceeded, excess $CH_2Cl_2$ leaving the bottom of the column via the filter layer (sinter) of the lower end cell 3' and the corresponding mobile phase port was recycled along the recycle line 19 to the $CH_2Cl_2$ supply vessel 13.

FIG. 5 is an axial cross-section view of the ejector used in the large-scale apparatus. The ejector is made from stainless steel, and has an outer tubular T-module 301 connected at one end to the pressurised fluid line 16, at the opposite in-line end to the downstream feed line 18 leading to the column and at the transverse T-line to the suction conduit 17 leading to the slurry tank. The connections are by conventional unions 160, 170, 180. The motive flow from the pressure line 16 passes to a restricted high-velocity nozzle 303 which opens into a wider cross-sectional area region adjacent the junction with the suction line 17. A short distance downstream of the nozzle 303 the flow re-enters an in-line narrow cross-section region of a divergent diffuser component 305 which returns the flow cross-section gradually to the original value.

The fluid-mechanical mechanism whereby the transition of a high-speed flow from the nozzle 303 into a wider cross-sectional area region entrains with suction the flow from the suction line 17 is well known and need not be discussed further here. No special considerations are involved. The function of the diffuser region 305 is to restore the flow to the lesser velocity and higher pressure prevailing in the main feed conduit 16 with minimal loss of flow energy.

Packing parameters included the following.

| | |
|---|---|
| Packing Flow Rate | 640 cm (linear)/hour (equivalent to 30 liters/minute) |
| Pressure of system at 30 liters/minute | 0.5 bar |
| Time to pack the column | not more than 1 hour. |

Note that the packing flow rate is substantially higher than the process flow rate used for chromatography—113 cm (linear)/hour in our test—so that the degree of compression of the bed is sufficient to avoid shifting during subsequent chromatography.

Thus, in the first place this method enables a column to be packed using a medium and liquid vehicle combination which by the normal pumping techniques could not be packed at all. Secondly, the fact that the medium is not subjected to the action of a mechanical pump means that the particles are less damaged by the packing process. This leads to a lower proportion of silica fines in the packed bed and better flow in the resulting chromatography.

What is claimed is:

1. A method of packing particulate chromatography medium into a chromatography column through a packing port in the column wall, comprising providing a feed conduit and a medium supply conduit, the feed conduit leading to the packing port and having a flow junction at an ejector, and the medium supply conduit meeting the feed conduit at the flow junction provided by the ejector;

connecting a supply of particulate medium in a liquid vehicle to the medium supply conduit, and forcing a motive flow of a liquid vehicle along the feed conduit to provide a reduced-pressure fluid flow zone at the ejector entraining in the motive flow a flow of the particulate medium dispersion from the medium supply conduit and carrying it into the chromatography column through the packing port.

2. A method as claimed in claim 1, in which said liquid vehicle for said supply of particulate medium and said liquid vehicle for said motive flow comprise the same liquid.

3. A method as claimed in claim 1, in which a mechanical pump upstream of the ejector drives the motive flow in the feed conduit.

4. A method as claimed in claim 3, in which the mechanical pump is a steady-output pump.

5. A method as claimed in claim 4, in which the pump is a centrifugal pump.

6. A method according to claim 5, in which the liquid vehicle is a non-polar organic solvent and the particulate medium is a normal-phase silica medium.

7. A method as claimed in claim 1, comprising recirculating liquid vehicle which re-emerges from the chromatography column during packing to a liquid vehicle supply for re-use in the packing method.

8. A method according to claim 1, in which the packing port has a spray nozzle and the dispersion of medium is sprayed into the column through the spray nozzle.

9. A method according to claim 1, in which the liquid vehicle is a non-polar organic solvent and the particulate medium is a normal-phase silica medium.

10. Apparatus adapted for carrying out a method of packing particulate chromatography medium as defined in claim 1, and comprising a pump for establishing a pressurized motive flow of a liquid vehicle;

a feed conduit connectable between the pump and a slurry port connection for communication through the wall of a chromatography column, to conduct said motive flow from the pump into the column;

a medium supply conduit, the medium supply conduit having an upstream connector for a medium supply vessel and a downstream connection into the feed conduit at a junction thereof, and an ejector provided in the feed conduit adjacent the junction with the medium supply conduit, positioned to provide a zone of reduced-pressure flow in said motive flow to entrain and a flow of a particulate medium dispersion along said medium supply conduit in use.

11. Apparatus according to claim 10, in which the pump is a centrifugal pump.

12. Apparatus according to claim 11, comprising a mobile trolley, said pump, connectors, conduits and ejector being mounted on said trolley.

* * * * *